United States Patent [19]

Kawanami et al.

[11] Patent Number: 5,532,494
[45] Date of Patent: Jul. 2, 1996

[54] TREATMENT AND OBSERVATION APPARATUS USING SCANNING PROBE

[75] Inventors: Yoshimi Kawanami, Kokubunji; Tsuyoshi Ohnishi, Katsuta, both of Japan

[73] Assignee: Hitachi, Ltd., Japan

[21] Appl. No.: 222,945

[22] Filed: Apr. 5, 1994

[30] Foreign Application Priority Data

Apr. 7, 1993 [JP] Japan .................................. 5-080444

[51] Int. Cl.[6] .................... G01N 23/225; H01J 37/252
[52] U.S. Cl. ........................... 250/491.1; 250/492.21; 250/306; 250/307; 250/309
[58] Field of Search ............................... 250/491.1, 307, 250/310, 492.21, 306, 309

[56] References Cited

U.S. PATENT DOCUMENTS

| 4,071,759 | 1/1978 | Namae | 250/310 |
| 4,683,378 | 7/1987 | Shimase et al. | 250/491.1 |

FOREIGN PATENT DOCUMENTS

| 60-131748 | 7/1985 | Japan . |
| 1-209647 | 8/1989 | Japan . |
| 3-263746 | 11/1991 | Japan . |
| 4-149945 | 5/1992 | Japan . |
| 5-198282 | 8/1993 | Japan . |

OTHER PUBLICATIONS

Solid State Technology, May 1987, pp. 77–78.

*Primary Examiner*—Jack I. Berman
*Attorney, Agent, or Firm*—Fay, Sharpe, Beall, Fagan, Minnich & McKee

[57] ABSTRACT

A treatment and observation apparatus using a scanning probe observes a desired area of a sample, forms a first image, magnifies a part of the area to be observed of the sample to observe it, forms a second image, and relates addresses of pixels constituting the first image and addresses of pixels constituting the second image to absolute addresses on the sample. The pixels constituting the images correspond to the addresses on the sample, respectively, and accordingly the second image can be used to designate the area to be treated with the resolution of the second image. In another embodiment, a desired area of the sample is observed with the maximum magnification and its image data are stored. The image data are compressed and displayed on a display screen of the observed area. The stored image data are read out freely with reference to the display picture to form a display picture for designating the area to be treated.

32 Claims, 14 Drawing Sheets

MAP OF PIXELS IN SAMPLE
IMAGE DISPLAY WINDOW

MAP OF PIXELS IN SAMPLE IMAGE
IN WHOLE SCANNING AREA OF PROBE
WHITE PORTION CORRESPONDS TO
WINDOW OF FIG.3A)

MAP OF SCANNING POINTS IN WHOLE
SCANNING AREA OF PROBE
(WHITE CIRCLES CORRESPOND TO
PIXELS OF WINDOW OF FIG.3A)

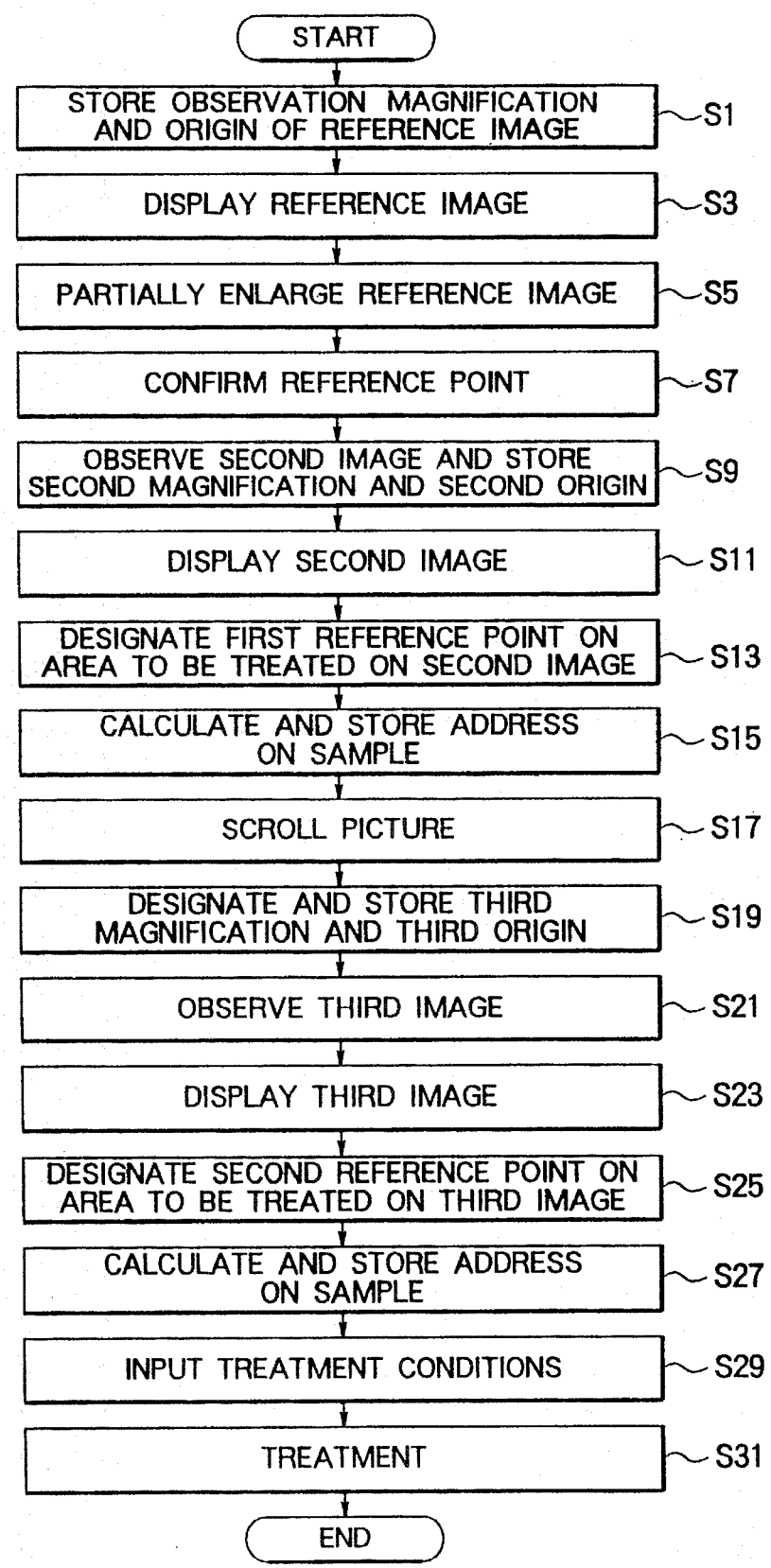

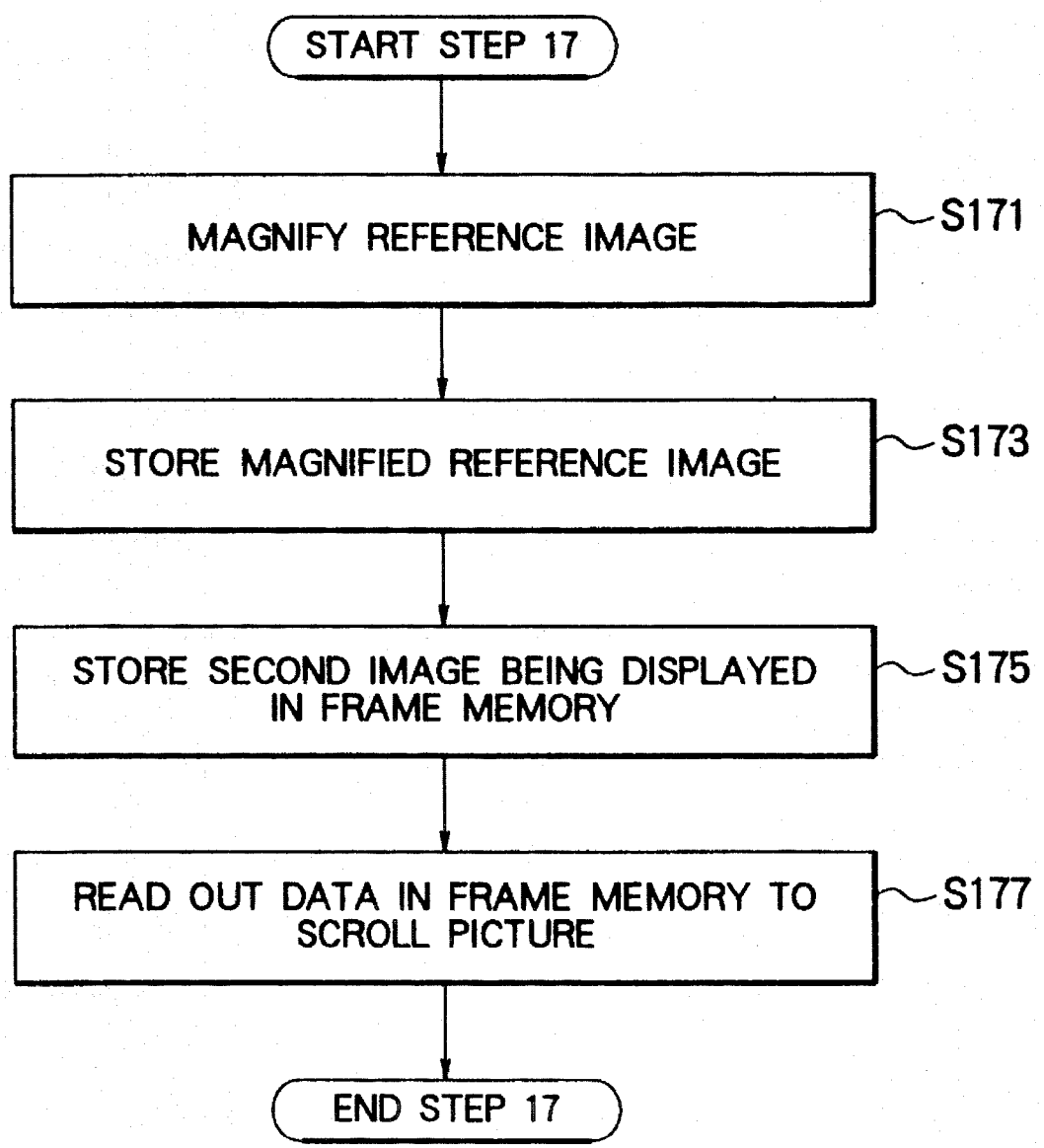

FIG. 10
→ NEW
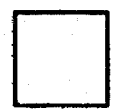  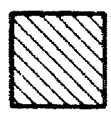 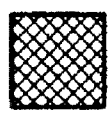 
×1    ×2    ×2    ×4    ×4
FIG. 11
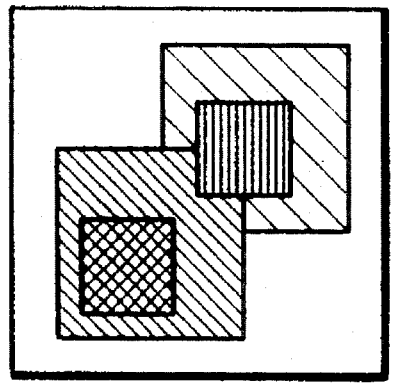
×4

TREATMENT AND OBSERVATION APPARATUS USING SCANNING PROBE

BACKGROUND OF THE INVENTION

The present invention relates to a treatment and observation apparatus using a scanning probe. As such an apparatus, there is known an apparatus utilizing a focused ion beam to observe and treat or work a semiconductor device.

An apparatus of this type using the focused ion beam as a probe is described in, for example, Solid State Technology, pp. 77–78, (May/1987). The apparatus uses secondary electrons obtained upon irradiation of the ion beam on a sample to form an image of the sample. A sample area to be treated is designated on a display screen on which the image is displayed. The area to be treated is irradiated with an ion beam under conditions different from an observation mode and is treated in accordance with a purpose.

In the apparatus, one point on the sample designated by an address is irradiated with the ion beam constituting a probe. When the address is changed, the ion beam is directed to a point designated by the changed address to irradiate the point with the ion beam. An address of a pixel on a display screen on which an image to be observed is displayed is in one-to-one correspondence to the address specifying the irradiation point of the probe on the sample.

In the treatment mode, the area to be treated is designated on the display screen on which the observation image is displayed as described above, and the address of the pixel on the display screen corresponds to the address on the sample. Accordingly, the designation accuracy of the area to be treated depends on the resolution of the display screen on which the observation image is displayed. In other words, a unit of a pixel on the display screen is a minimum unit for designating the area to be treated. Accordingly, the treatment accuracy is specified by a magnification of the observed image. In this connection, as a space or gap between two adjacent points designated by addresses on the sample becomes smaller, the magnification upon observation becomes larger and the treatment accuracy becomes higher.

In the conventional apparatus, since a larger area to be treated is designated by using the observed image having a low magnification, the treatment accuracy can be ensured.

SUMMARY OF THE INVENTION

It is an object of the present invention disclosed in the specification to provide a treatment and observation apparatus using a scanning probe capable of ensuring fixed treatment accuracy regardless of a size of an area to be treated.

According to one aspect of the present invention, an observed image of a sample having a low magnification and including the whole area to be treated is formed as a reference image. The origin of the reference image is related to one address on the sample. In an embodiment, a reference point on the sample irradiated with an ion beam which is in a neutral state or which is not deflected is adapted to coincide with the origin of the reference image. The observation magnification of the reference image is a first basic magnification and its shift data is (0, 0).

In the present invention, an observation mode is carried out again with reference to the reference image and a portion of interest of the reference image; for example, a portion requiring minute treatment or an edge of an area to be treated of the reference image is magnified and observed. Thus, a second image is formed. At this time, addresses of pixels on the second image are caused to correspond to addresses on the sample because of a two-dimensional shift amount of the origin of the second image to the origin of the reference image and a difference in a magnification between the second image and the first image. Since the second image is obtained by observation with larger magnification than that of the reference image, the addresses of pixels of the second image correspond to points having addresses in the sample designated with a pitch smaller than that of the first image. Accordingly, the second image is used to designate an area to be treated, to thereby perform treatment with higher accuracy.

The second image is a partially magnified image of the reference image and accordingly there is a case in which the whole area to be treated cannot be covered by means of a single second image. When an area required to be observed with large magnification is included in an area which is not covered by the second image, the reference image is displayed again and the same operation as the above is repeated to form a third image.

According to a second aspect of the present invention disclosed in the specification, the third image can be formed easily.

The reference image is magnified to an image with the same magnification as the observation magnification of the second image, and the image with the same magnification is combined with the second image to store the combined image in an image memory. First, the second image, appears on the display screen, while when the image on the display screen is scrolled, the combined image is successively read out from the image memory to be displayed on the display screen. An operator can follow the magnified reference image subsequent to the second image and reach a portion to be desired correctly and rapidly. Thus, the third image of the portion is observed. When the second image is combined with the reference image, the shift data of the second image and a ratio of the observation magnification of both the images are required.

According to a third aspect of the present invention, the whole area of the sample corresponding to the reference image is observed with the maximum magnification, and data thereof are stored in a memory having a large capacity. If the data is to be displayed in the display unit in one-to-one correspondence, a huge display unit would be required, but which is not actually employed. Similarly to the first aspect, the addresses of the data in a large capacity memory and the addresses on the sample have one-to-one correspondence. The data in the large-capacity memory are compressed by a known method and displayed on the display screen of a conventional display unit. Accordingly, one address on the display screen of the display unit corresponds to an address of a plurality of data in the memory. When the compressed data image is used as the reference image, a desired portion or area can be magnified by using the data in the large capacity memory. Since the addresses of pixels on the magnified image configured above correspond to the addresses of the data in the large capacity memory, the addresses on the display screen of the magnified image correspond to the addresses on the sample. Accordingly, the area required to be treated can be designated by means of the magnified image to thereby be treated with high accuracy corresponding to the resolution of the magnified image.

In a preferred embodiment, a focused ion beam is utilized by way of example, while the present invention is applicable to an apparatus having a probe such as not only an electronic beam apparatus and an optical beam apparatus but also an STM and the like in accordance with characteristics of the sample, a purpose for treatment or the like.

Another method of relating addresses of pixels on the display screen to addresses on the sample on the basis of the magnification and shift amount is now described.

(1) Relation of the Resolution of a Display Window and the Resolution of a Scanning Point The address resolution of the scanning point of the probe is increased by the integral power of 2 (2^Nmax) as compared with the address resolution of pixels in the display window for a sample image.

More particularly, when the number of each of the addresses (X, Y) of the scanning points is 2^Nd and the number of each of the addresses (x, y) of pixels in the display window is 2^Np, the following equation is formed:

$$Nd = Np + Nmax \quad (1)$$

where Nd, Np and Nmax are positive integers.

In the example shown in FIGS. 3A and 3C, since Nd is 4 and Np is 2, Nmax is 2.

(2) Relation of the Display Window and the Whole Sample Image

The sample image in the whole scanning area of the probe is previously prepared in accordance with the magnification designation (2^N) and a part of the whole sample image is displayed in the sample image display window in accordance with the shift designation (xs, ys).

More particularly, when the number of each of the addresses (x', y') of pixels of the whole sample image is 2^Nv, a value of each pixel of the whole sample image is U(x', y') and a value of each pixel of the display window is I(x, y), the following equations are formed:

$$I(x, y) = U(x+xs, y+ys) \quad (2)$$

$$Nv = Np + N \quad (3)$$

where xs and ys are integers and N and Nv are positive integers. N is to satisfy the following equations:

$$0 \neq \leq N \neq \leq Nmax \quad (4)$$

In the example shown in FIG. 3B, the shift amounts xs and ys are 0 and 1, respectively. The magnification 2^N is 2.

(3) Relation of the Display Window and the Sample Image

Addresses of pixels in the sample image have one-to-one correspondence to those in the sample image display window. The obtained sample image is stored together with the magnification designation and the shift designation at that time but is not displayed in the sample image display window directly.

More particularly, in order to obtain the sample image, a series of scanning points of addresses (X, Y) corresponding to addresses (x, y) of pixels of the sample image are irradiated with the probe in accordance with the following equations and secondary particle signals from the respective scanning points are stored as values of pixels of the corresponding sample image.

$$X = (x+xs)P + C$$

$$Y = (y+ys)P + C \quad (5)$$

where P and C are values related to the magnification and are defined as follows:

$$P = P(N) = 2^{\wedge}(Nmax-N)$$

$$C = C(P) = (P-1) \text{ div } 2 \text{ or } 0 \quad (6)$$

In the example shown in FIGS. 3A to 3C, C(P) is always 0.

(4) Relation of the Whole Sample Image Stored and the Sample Image

The sample image of the whole scanning area of the probe is prepared when the magnification designation is changed or when the sample image is obtained newly. Further, the whole sample image is prepared by combining the sample images stored so far.

(5) Designation and Display Method of an Area to be Treated

Designation of the area to be treated is represented by a set of addresses of the scanning points, while in order to establish the designation of the area from the sample image display window, addresses of pixels of the sample image display window are caused to uniquely correspond to addresses of the scanning points in accordance with the equation (5).

In addition, in order to display the designation of the area to be treated on the sample image display window, the addresses of the scanning points are caused to correspond to the addresses of pixels of the sample image display window in accordance with the following equations. (When there is no corresponding address, it is not displayed.)

$$X + k = x'P + C = (x+xs)P + C$$

$$Y + k = y'P + C = (y+ys)P + C \quad (7)$$

where k is an integer and satisfies the following conditions:

For $P > 1$, $-C \neq \leq k \leq -C + (P-1)$

For $P = 1$, $k = 0 \quad (8)$ (6) Preparing Method of the Whole Sample Image

In order to prepare the sample image of the whole scanning area of the probe, sizes of the stored sample images are changed in accordance with the accompanying magnification designation, and the sample images having the changed sizes are superposed on each other so that a newer sample image is overlaid on another in accordance with the accompanying shift designation.

More particularly, the sample image stored in the j-th order is Tj(x, y), the magnification designation accompanying the sample image is 2^Nj, and the shift designation is (xsj, ysj). Then, after Tj(x, y) is converted into Uj(x', y') by the following method, a newest of Uj(x', y') which is not 0 (that is, smallest of j) is the whole sample image U(x', y'). Thus, if (x, y) satisfying the following conditions (a) to (c) does not exist, Uj(x', y') is 0; and if it exists, it is as follows:

$$Uj(x', y') = Tj(x, y) \quad (9)$$

(a) In the case of Nj=N $$x' = x + xsj$$

$$y' = y + ysj \quad (10)$$

(b) In the case of Nj>N $$x'P+C=(x+xsj)Pj+Cj$$

$$y'P+C=(y+ysj)Pj+Cj \quad (11)$$

(c) In the case of Nj<N $$(x'+k)P+C=(x+xsj)Pj+Cj$$

$$(y'+k)P+C=(y+ysj)Pj+Cj$$

$$-Cj \neq \leq kP < -Cj+(Pj-1) \quad (12)$$

In the above, k is an integer and Pj and Cj are defined as follows:

$$Pj=P(Nj)$$

$$Cj=CP(Pj) \quad (13)$$

where the equation (11) for the condition (b) may be replaced by the following equation (14). However, since a plurality of (x, y) satisfy the condition in this case, an average value of Tj(x, y) is required to be a value of Uj(x', y').

$$x'P+C=(x+k+xsj)Pj+Cj$$

$$y'P+C=(y+k+ysj)Pj+Cj$$

$$-C \neq \leq kPj < -C+(P-1) \quad (14)$$

BRIEF DESCRIPTION OF THE DRAWINGS

FIGS. 4A and 4B are flow charts showing the operation of the apparatus of the first embodiment;

FIG. 10 schematically illustrates a plurality of images having different magnification and shift data;

FIG. 11 illustrates combined image data of FIG. 10;

DESCRIPTION OF THE PREFERRED EMBODIMENTS

Embodiments of the present invention are now described.

Figure 1:
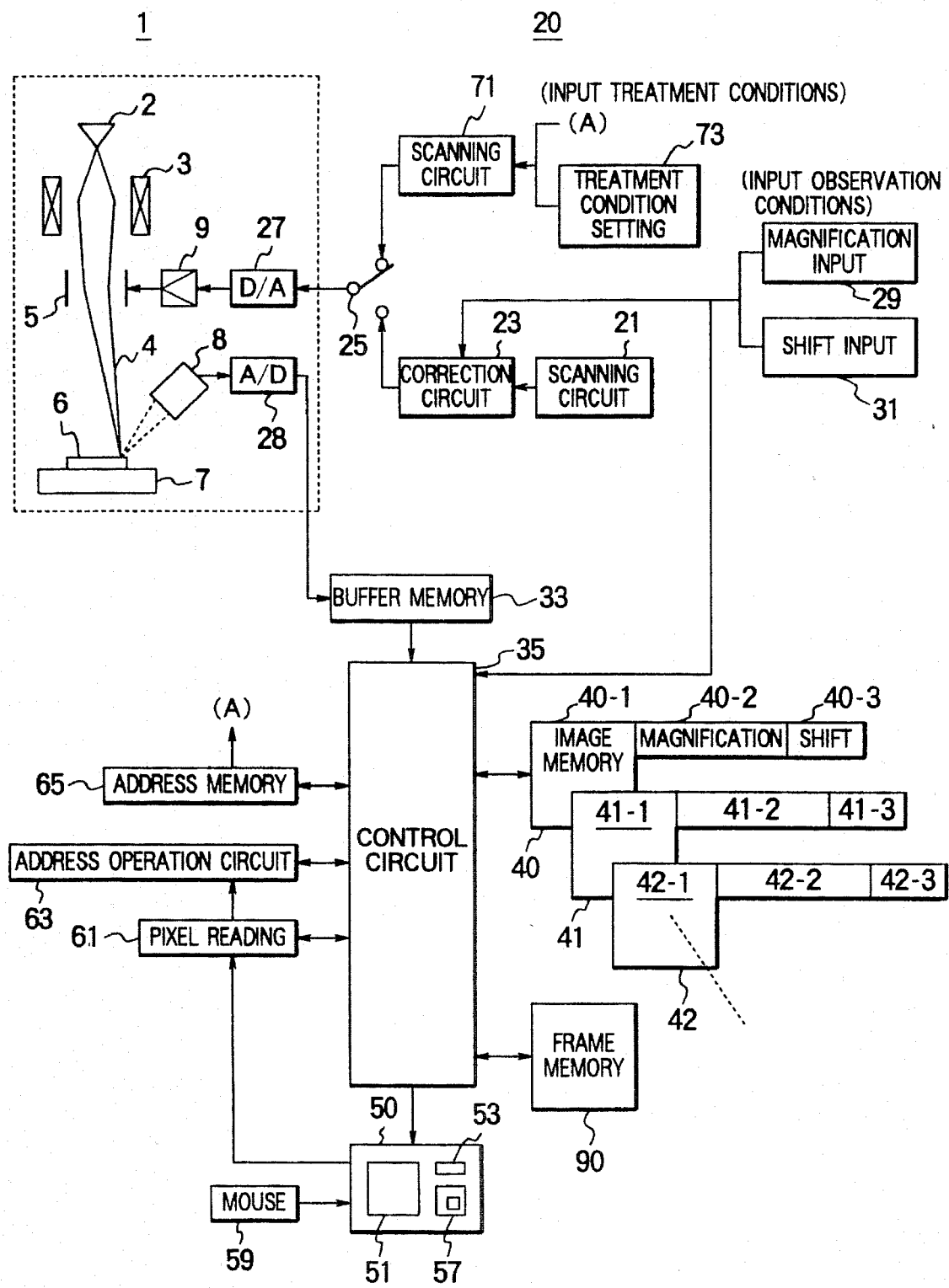
FIG. 1 schematically illustrates a treatment and observation apparatus according to a first embodiment of the present invention.

FIG. 1 schematically illustrates a treatment and observation apparatus using a focused ion beam according to a first embodiment.

The treatment and observation apparatus of the first embodiment comprises a beam scanning apparatus 1 and a controller 20. The beam scanning apparatus 1 includes an ion source 2. A lens system 3 serves to extract ions from the ion source 2 and form a beam 4. A deflection system 5 deflects an irradiation position of the beam 4 on a sample 6. The sample 6 is held on a stage 7 and the stage 7 can move the sample 6 horizontally. Further, the stage 7 can incline the sample 6 if necessary. When the sample 6 is irradiated with the beam, secondary electrons are emitted from the surface of the sample 6 and are captured by a detector 8, and the captured secondary electrons are converted into a digital signal by an A/D converter 28. Numeral 9 denotes an amplifier which amplifies a signal supplied from the controller 20.

Figure 2:
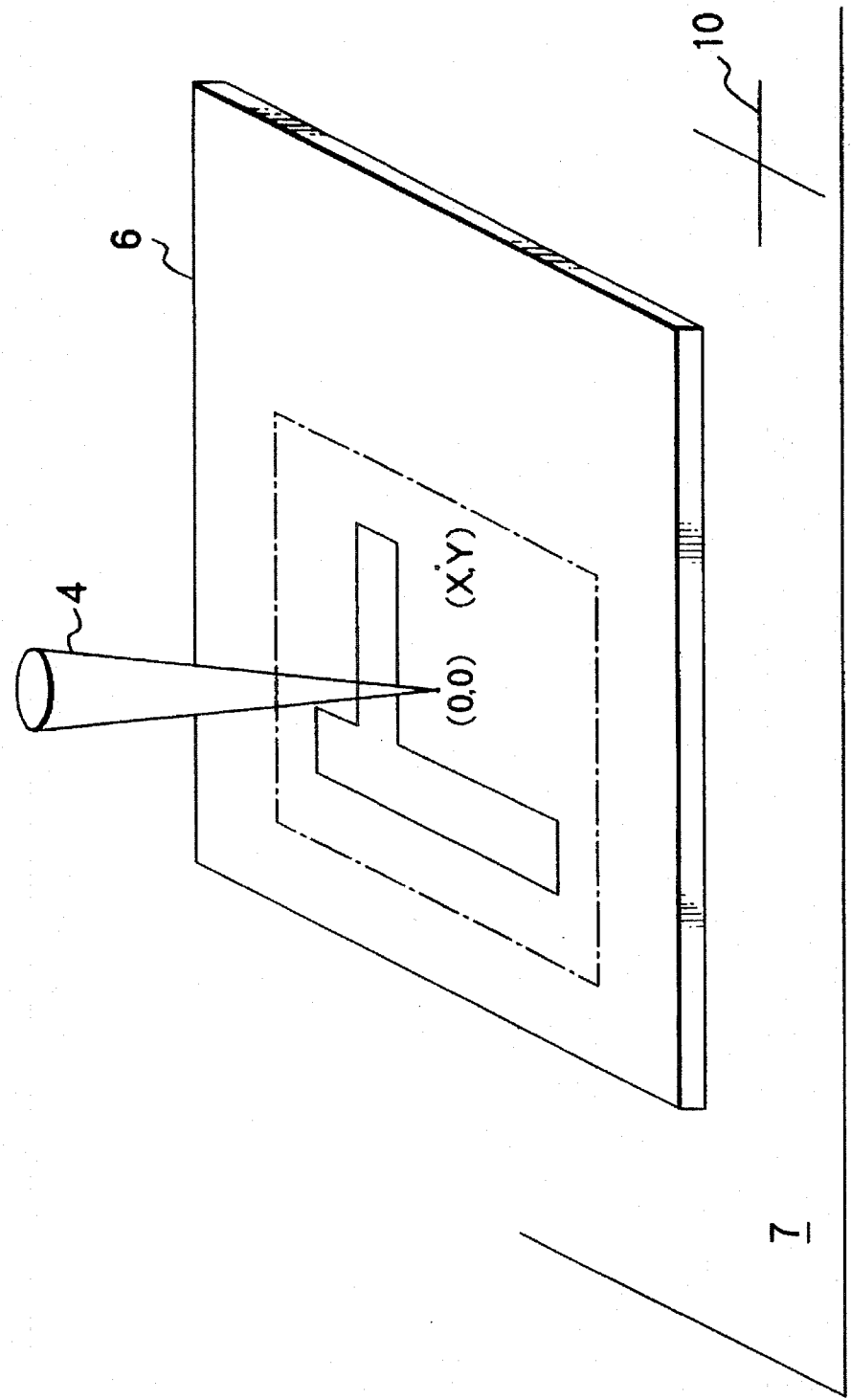
FIG. 2 illustrates a relation of addresses on a sample and a beam.
Figure 3A:
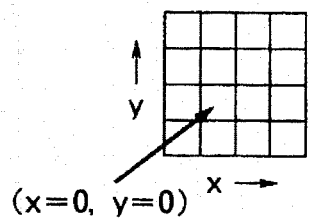
FIGS. 3A, 3B and 3C illustrate correspondence of addresses of pixels on a display screen and addresses on a sample.
Figure 3B:
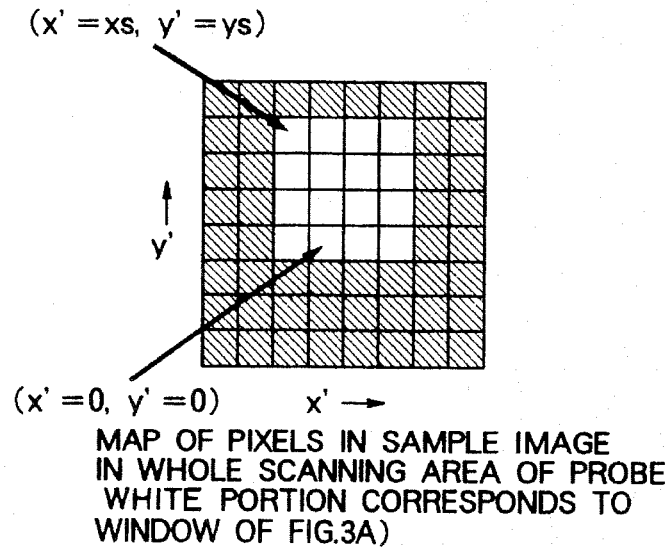
Figure 3C:
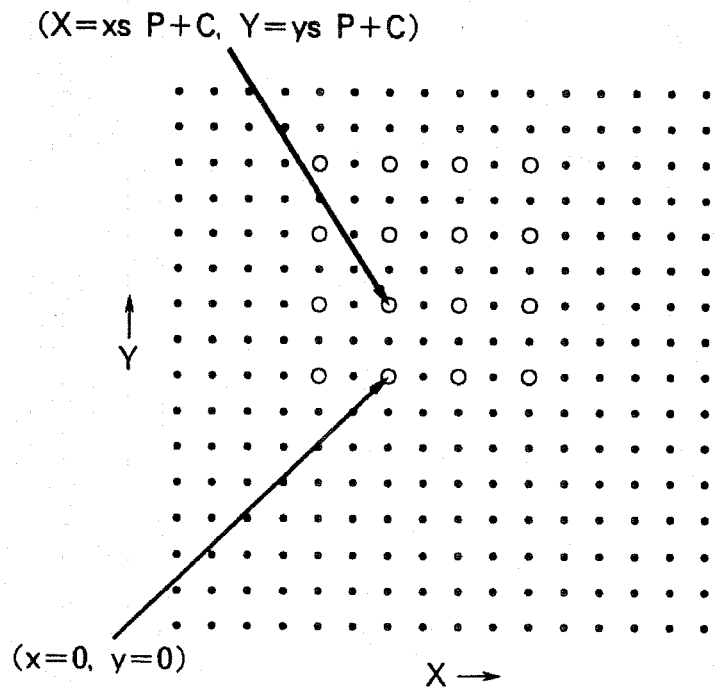

In this beam scanning apparatus 1, when a signal supplied to the deflection system 5 is neutral, that is, when the beam is not deflected, a point on the sample irradiated with the beam 4 is a reference point (0, 0) (refer to FIG. 2). When a signal is supplied from the controller 20 to the deflection system 5, the beam is deflected to a point (X, Y) on the sample corresponding to the signal. The signal designates an address for this point. A reference mark 10 is formed on the stage 7. By irradiating the reference mark 10 with the beam 4, a shift of the reference point is detected and the shift is corrected if necessary. A focused ion beam apparatus (type: FB4080 or FB2000) offered by Hitachi Corp. can be used for the beam scanning apparatus 1.

The controller 20 is now described.

A scanning circuit 21 produces a basic signal for raster scanning the beam. The signal designates an address corresponding to a pixel of a display screen. The signal is corrected by a correction circuit 23 and is supplied through a switch 25, a D/A converter 27 and the amplifier 9 to the deflection system 5. The correction circuit 23 is supplied with magnification and shift data from input units 29 and 31, respectively. The basic signal produced by the scanning circuit 21 is modulated in the correction circuit 23 in accordance with the inputted magnification and shift data. The magnification and shift data are also supplied to a control circuit 35 and stored in memories 40-2 and 40-3, respectively.

When the inputted magnification is one time ($2^0$ time), the beam is deflected largest, so that the maximum area capable of being irradiated with the beam is observed on the sample. In this state, the space or pitch of addresses on the sample irradiated with the beam is maximum. In this embodiment, the magnification is $2^n$, where n can be inputted as an integer from 0 to 10. For example, when the magnification of $2^k$ is inputted, the space of addresses on the sample is $\frac{1}{2^k}$ of that in the case where the space of addresses on the sample is one time ($2^0$ time), so that a length of one side of the observation area is $\frac{1}{2^k}$ times smaller. When such an observation area is displayed in the display screen having a fixed size, the image is magnified $2^k$ times.

Since the controller 20 of the embodiment is required to control the irradiation position of the beam more minutely, the magnification can be designated by $2^n$, while it is a matter of course that the magnification may be designated by $3^n, 4^n, 5^n, \ldots, N^n$ (where N and n are integers). When the shift data are inputted by the input unit 31, an address ($X_1$, $Y_1$) corresponding to the shift data is determined. A second image is observed about the address ($X_1$, $Y_1$). The observation area of the second image is automatically determined on the basis of the magnification designated at this time and the number of pixels on the display screen of the display unit. It should be noted that addresses on the sample irradiated with the beam have one-to-one correspondence to addresses of pixels on the display screen.

In the observation mode, signals detected by the detector 8 are successively supplied to a buffer memory 33 via an A/D converter 28 in synchronism with a timing of the scanning circuit 21. The control circuit 35 prepares image data from the data stored in the buffer memory 33 and stores the image data in an image memory 40-1. The magnification and shift data of the observation are stored in a magnification memory 40-2 and a shift memory 40-3 in relation to the image memory 40-1, respectively. The control circuit 35 sends the image data, the magnification data and the shift data to a display unit 50 to display the data on the display unit. The image data are displayed on a display screen 51, the magnification data are displayed on a display screen 53, and the observation area is displayed on a display screen 57.

A cursor displayed on the display screen 51 can be moved by a mouse 59 to thereby designate a desired pixel. An address of the designated pixel is read out by a reading unit 61. An address operation circuit 63 specifies a corresponding address on the sample from the address of the read pixel with reference to the magnification data and the shift data. The specified address on the sample is stored in an address memory 65. This address is supplied to a scanning circuit 71 through a path shown by (A) of FIG. 1 in the treatment mode.

In the treatment mode, the signal produced by the scanning circuit 71 is supplied to the deflection system 5 through the switch 25, the D/A converter 27 and the amplifier 9. The scanning circuit 71 includes a circuit for calculating all addresses capable of being designated on the sample contained in a rectangle defined by end points on a diagonal line determined by two addresses designated by the display screen 51. That is, in the treatment mode, the beam is scanned in a pitch corresponding to the maximum magnification in the observation mode.

Operation of the apparatus of the embodiment is now described with reference to FIG. 1, a flow chart shown in FIG. 4, and display screens of the display unit 50 illustrated in FIGS. 5 to 9. The area to be treated is a rectangular portion extending horizontally in a figure shown in a display screen 51-1 of FIG. 5.

In step 1, the stage 7 is freely moved to determine a position of the sample with respect to the beam 4. The sample is observed with a first desired magnification $2^k$ to obtain reference image data. At this time, an irradiation position (X=0, Y=0) of the beam in the neutral state on the sample corresponds to the origin (x=0, y=0) of the reference image. The obtained image data correspond to addresses on the sample irradiated with the beam 4. The reference image data are stored in the image memory 40-1. A first magnification inputted by the input unit 29 and the automatically determined origin (0, 0) of the reference image are stored in the magnification memory 40-2 and the shift memory 40-3, respectively.

Figure 5:
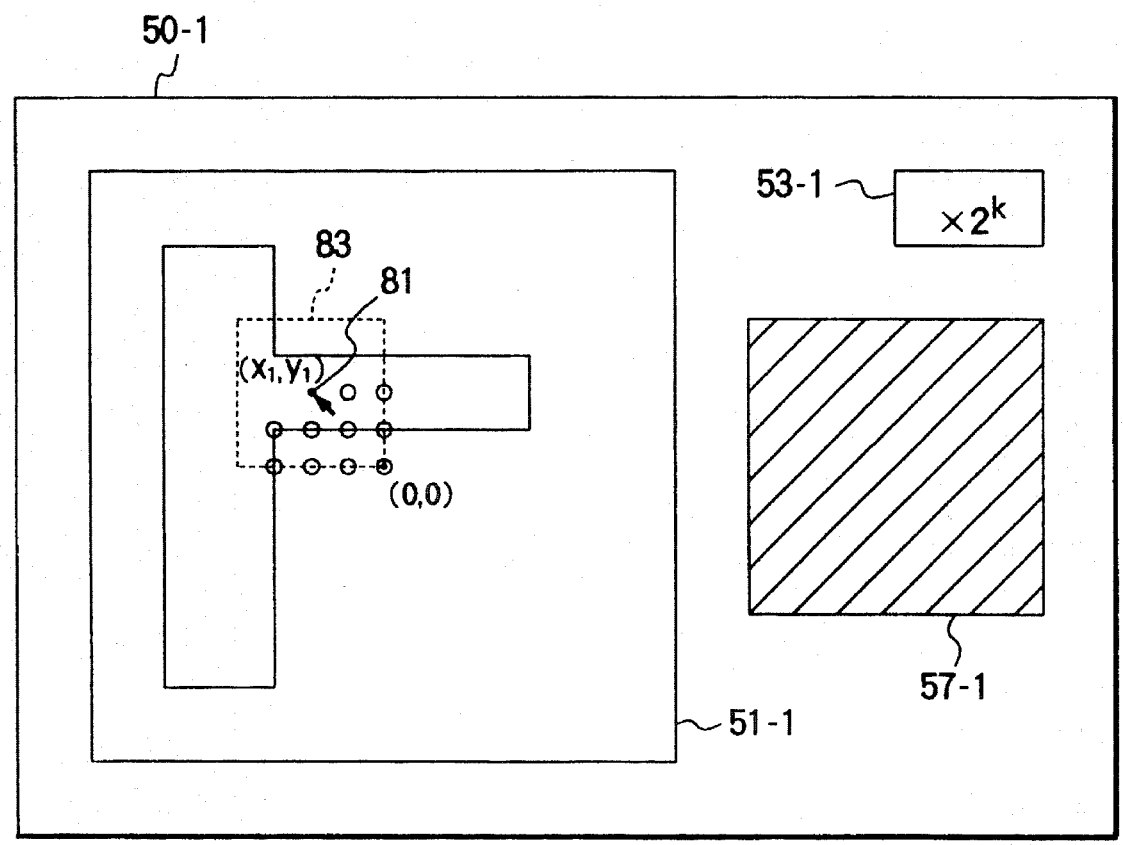
FIG. 5 illustrates a display screen or picture of a reference image.

In step 3, the reference image is displayed on the display screen 51 of the display unit 50 as shown in FIG. 5. Addresses (x, y) of pixels on the display screen 51-1 correspond to addresses of the image memory 40-1 and addresses of the memory correspond to addresses (X, Y) on the sample for a parameter of the magnification. Accordingly, the addresses (x, y) of the pixels correspond to the addresses (X, Y) on the sample. The addresses of pixels on the display screen are caused to correspond to the addresses on the sample by the address operation circuit 63. The first magnification is displayed on display screen 53-1 and the observation area is displayed on display screen 57-1. Since images described later are observed for the reference of the area of the reference image, the whole area of the display screen 57-1 is a display area.

Figure 6:
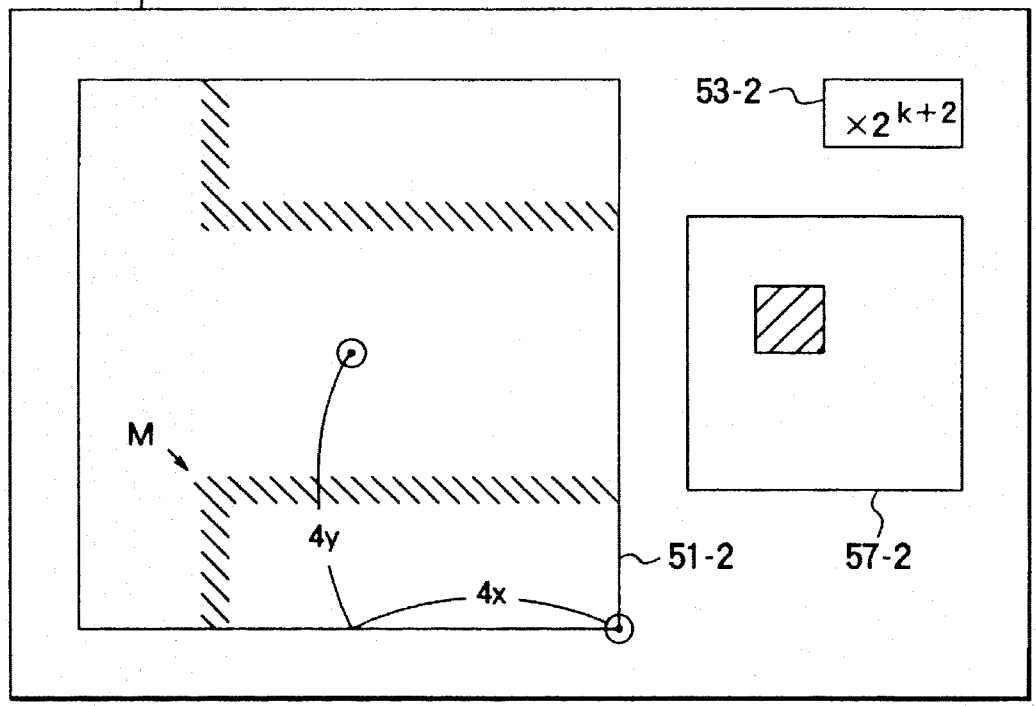
FIG. 6 illustrates a partially magnified image of the reference image.

In step 5, the reference image is partially magnified. A cursor 81 is moved at the center of a portion to be magnified in the display screen 51-1 of FIG. 5 before magnifying the reference image. An address (X1, Y1) on the sample is calculated by the operation circuit 63 from an address (x1, y1) of a pixel to which the cursor is moved. The address (X1, Y1) on the sample becomes a first shift datum and is accordingly stored in a register not shown in the control circuit. When the magnification of $2^{k+2}$ is inputted, a magnified and displayed area is displayed by broken line 83. As described above, since there is a limitation to the magnitude of the display screen 51-1, a magnifiable area is automatically restricted in accordance with the magnification. Thereafter, when the magnification process is carried out, a picture shown in FIG. 6 appears. This process is carried out by the control circuit 35 in a known manner. Outlines of the image are expressed thick in the picture 51-2 of FIG. 6. Accordingly, the resolution of FIG. 6 is the same as that of FIG. 5. In the picture 51-2 of FIG. 6, the first origin of the reference image is coincident with an apex or corner at the right lower portion. The area surrounded by broken line in the display screen 51-1 of FIG. 5 is displayed in the display screen 57-2. The designated magnification $2^{k+2}$ is also stored in the register of the control circuit.

In step 7, it is confirmed that a noticeable point in the area to be treated, that is, a point M which is one reference point of the area to be treated in this case, has appeared on the picture 51-2.

In step 9, observation is performed about the second origin (X1, Y1) with the second magnification $2^{k+2}$ again. This observation is performed by modulating the reference signal from the scanning circuit 21 by the correction circuit 23 as described above. The second image data thus obtained are stored in the image memory 41-1. Further, the second origin (X1, Y1) and the magnification $2^{k+2}$ designated temporarily in step 5 are settled. Thus, the second origin and the magnification are both stored in the shift memory 41-3 and the magnification memory 41-2.

Figure 7:
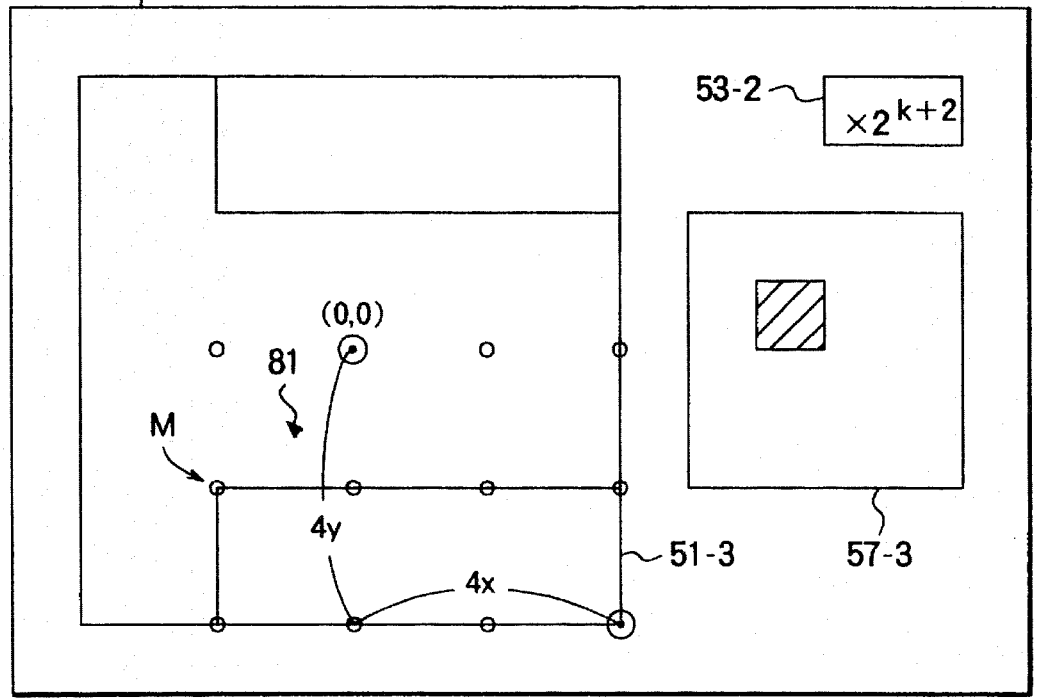
FIG. 7 illustrates a second image.

In step 11, the second image is displayed in a picture 51-3 as shown in FIG. 7. The marks (○) in the pictures 51-1 and 51-3 indicate the magnified state and do not appear in the actual picture. It can be understood from FIG. 5 that the origin (x, y)=(0, 0) of the picture 51-3 corresponds to (X1, Y1) on the sample. Similarly, the addresses of pixels on the picture 51-3 correspond to the addresses on the sample. Since the second image is observed with larger magnification as compared with the reference image and the addresses on the sample are designated more minutely, some of the addresses on the sample corresponding to the pixels on the picture 51-3 do not correspond to pixels on the picture 51-1.

In step 13, the first reference point M for treatment is designated in the second image. More particularly, the cursor 81 is operated by the mouse 59 to designate the point M.

In step 15, the address (xM, yM) of the point M on the picture 51-3 is read by the pixel reading unit 61 and the address (XM, YM) on the sample corresponding to the address (xM, yM) is calculated by the address operation circuit 63. As described above, the shift data and the magnification stored in the memories are referenced in the operation. The calculated address (XM, YM) on the sample is stored in the memory 65.

In step 17, contents of the picture are scrolled. This step is described in detail in the flow chart of FIG. 4B.

The control circuit 35 reads out the reference image data stored in the image memory 40-1 and magnifies the reference image data to the same magnification as that of the second image (four times in the embodiment) and stores the magnified reference image data in the frame memory 90 (steps 171 and 173). In step 175, the second image data being displayed are stored in the frame memory 90 similarly. At this time, the portion corresponding to the second image in the magnified reference image is replaced by the data of the second image. Thus, the two images are combined in the frame memory. Further, if the address of the origin of the frame memory 90 is caused to be coincident with the address of the origin of the reference image, alignment of the reference image and the second image is performed with reference to the respective shift data and magnification. It is also understood that the addresses of the frame memory 90 correspond to the addresses on the sample. More particularly, by aligning the origin of the second image with the origin of the picture 51-2 of FIG. 6, the two images are combined.

Figure 8:
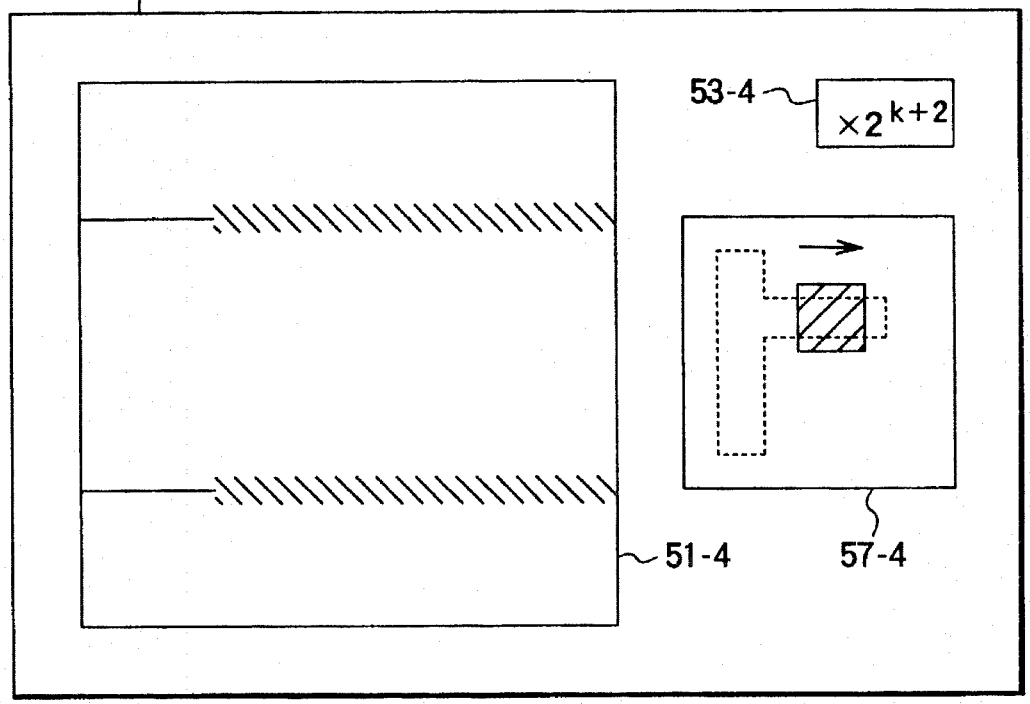
FIG. 8 illustrates a scrolled picture content.

In step 177, data in the frame memory 90 are successively read out to thereby scroll the contents of the picture. FIG. 8 shows the display area shifted right. In a picture 51-4 of FIG. 8, solid lines indicate part of the second image and oblique line portions indicate part of the magnified reference image. In this manner, the contents of the picture are scrolled, and, when the right end of the area to be treated appears in a substantially central portion of the picture 51-4, the scrolling is stopped.

Figure 9:
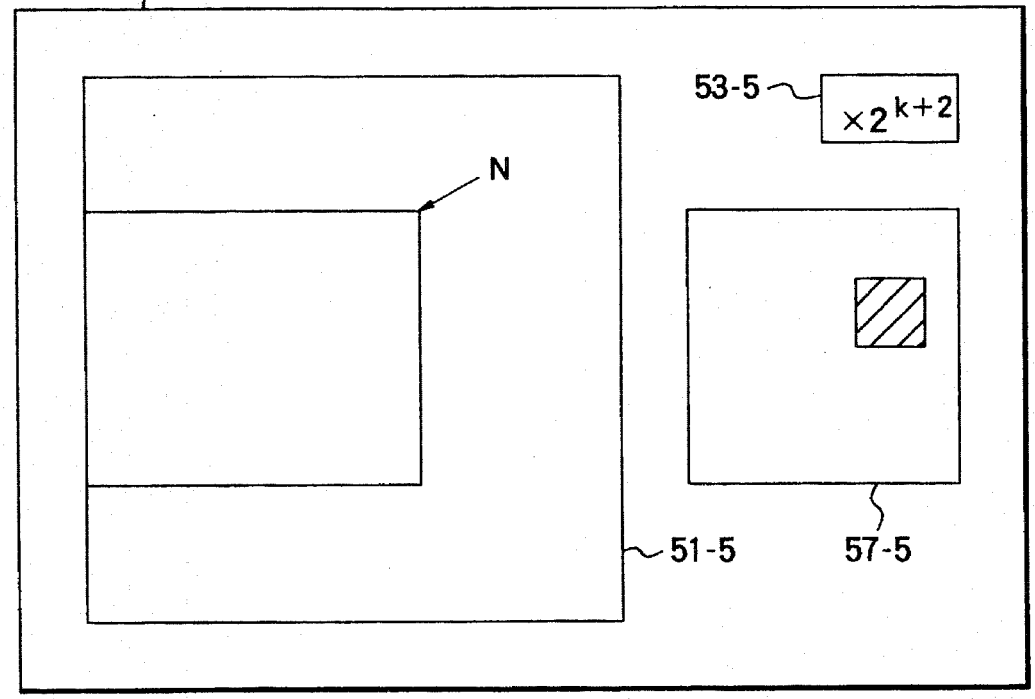
FIG. 9 illustrates a third image.

Since the addresses of pixels on the picture 51-4 correspond to the addresses on the sample through the addresses of the frame memory 90, the same operation as in steps 7 to 11 is performed to thereby observe a third image and display it as shown in FIG. 9 (steps 19 to 23). The address on the sample for a second reference point N on the area to be treated is also stored in the memory 65 by the same operation as in steps 25 and 27.

In step 29, treatment conditions are set by the setting device 73. The treatment conditions are set in accordance with characteristics of the sample and the purpose of treatment. In this embodiment, the irradiation time of the beam is made longer than that in the observation mode.

In step 31, the scanning circuit 71 calculates addresses contained in a rectangular area defined by end points on one diagonal line determined by the reference points M and N on the sample. The addresses correspond to addresses designated when the beam is scanned with the maximum magnification in the observation mode.

In this embodiment, the reference point of the area to be treated is defined in the reference image whose magnification is shown in FIG. 6, while the reference point can be designated in the reference image itself shown in FIG. 5. The method of designating the area to be treated is not limited to the method using the two reference points as described above, while all outlines of the area to be treated may be designated. Further, in the second and third images, all addresses contained in the area to be treated can be also designated by painting out the area to be treated.

In this embodiment, when the contents of the picture are scrolled as in FIG. 8, a combination of the reference image and the second image is used. According to the apparatus of the embodiment, since the observed image is stored together with the magnification and the shift data thereof, even three or more images can be combined similarly, and the combined image can be scrolled in the picture. FIG. 10 schematically illustrates a plurality of observed images having different shift data together with the magnification of observation thereof. FIG. 11 schematically illustrates a combined image thereof. In the combined image of FIG. 11, a newly observed image is superposed on older images.

Figure 12:
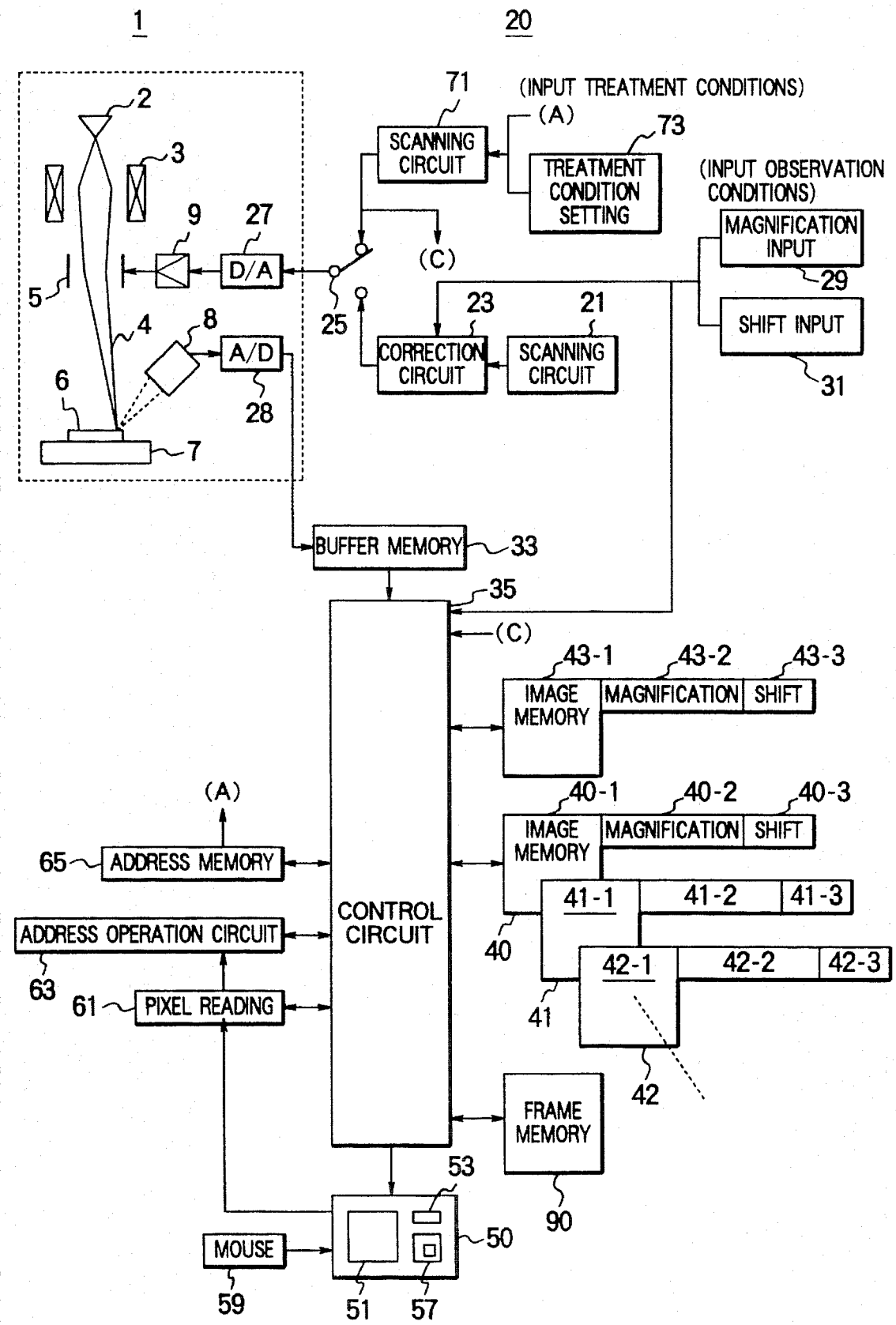
FIG. 12 schematically illustrates a treatment and observation apparatus according to a second embodiment of the present invention.

FIG. 12 schematically illustrates a treatment and observation apparatus according to another embodiment. Like elements to those of FIG. 1 are designated by like reference numerals and description thereof is partially omitted.

The apparatus pays attention to the fact that the same beam as in the observation mode is used in the treatment mode and is to form an image even in the treatment mode. It should be noted that in FIG. 12, a memory 43 is added and the scanning circuit 71 for treatment is connected to the control circuit 135 by means of a bus line (C) as compared with FIG. 1.

Figure 13:
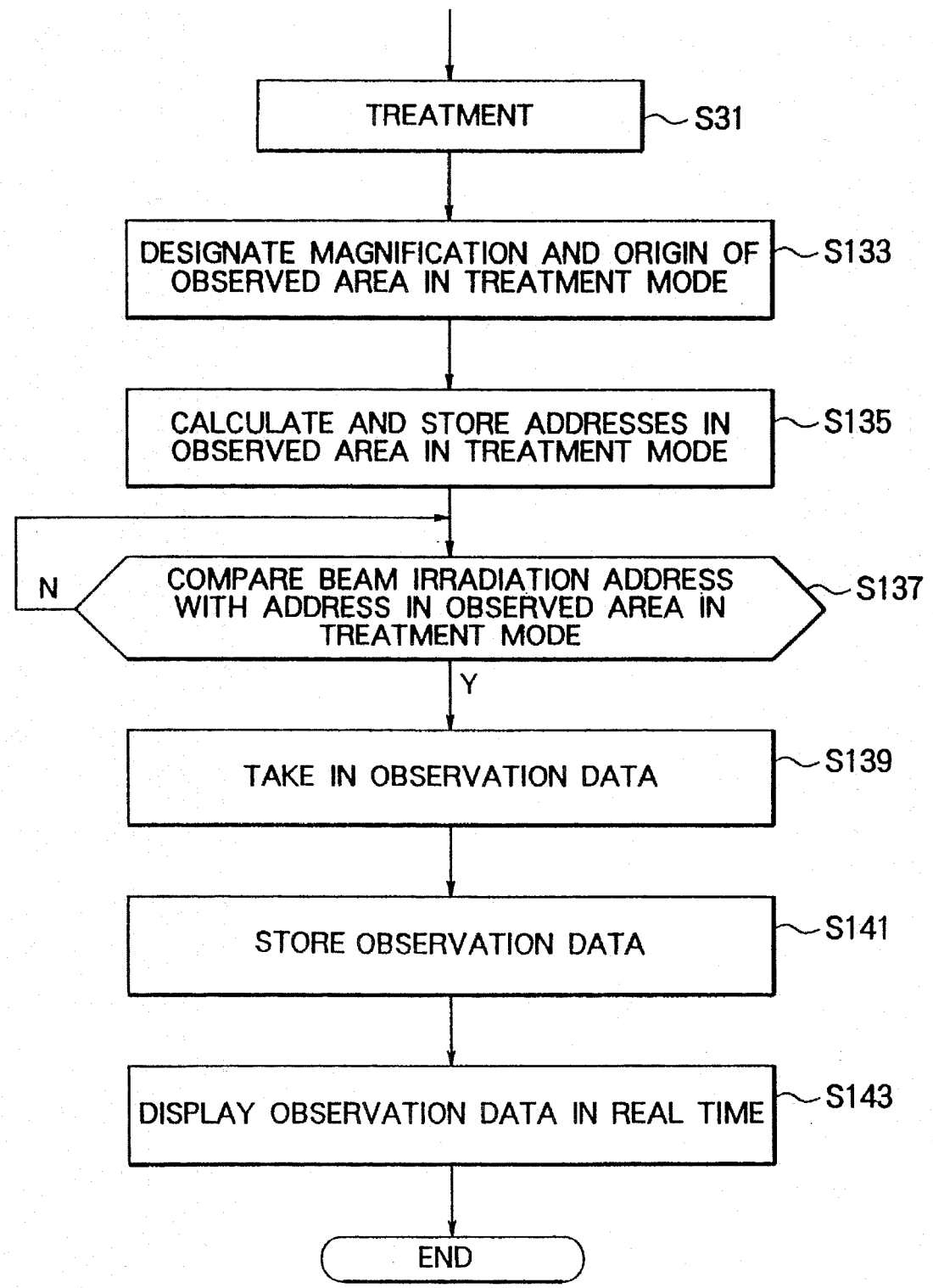
FIG. 13 is a flow chart showing the operation of the apparatus according to the second embodiment.

FIG. 13 shows the operation of the embodiment. In the flow chart of FIG. 13, the operation performed before step 31 is the same as the operation performed in the same steps in FIG. 4A. In step 133, designation of the observation magnification and the origin of the observation area is required. The designation is performed using the reference image in the same manner as in the observation mode, and the observation magnification and the origin of the observation area are stored in memories 43-2 and 43-3, respectively. The control circuit 35 calculates all addresses on the sample covered by the observed area in the treatment mode on the basis of the magnification and the observed area and stores them in an internal memory of the control circuit (step 135). In the treatment, secondary electrons emitted from addresses on the sample irradiated with the beam are captured by the detector 8 and are once stored in the buffer memory 33 via the A/D converter 28. The control circuit 13 reads in the output signal of the scanning circuit 71 and compares addresses on the sample designated by the output signal with addresses of the observation area in the treatment mode stored in the internal memory (step 137). When both of the addresses are identical, data in the buffer memory 33 are taken in (step 139) and are stored in the image memory 43-1 (step 141). Thus, the image data in the area to be treated are stored in the image memory 43. Since the magnification and shift data are stored in relation to the image data in the area to be treated, the treated image can be superposed on another image.

Figure 14:
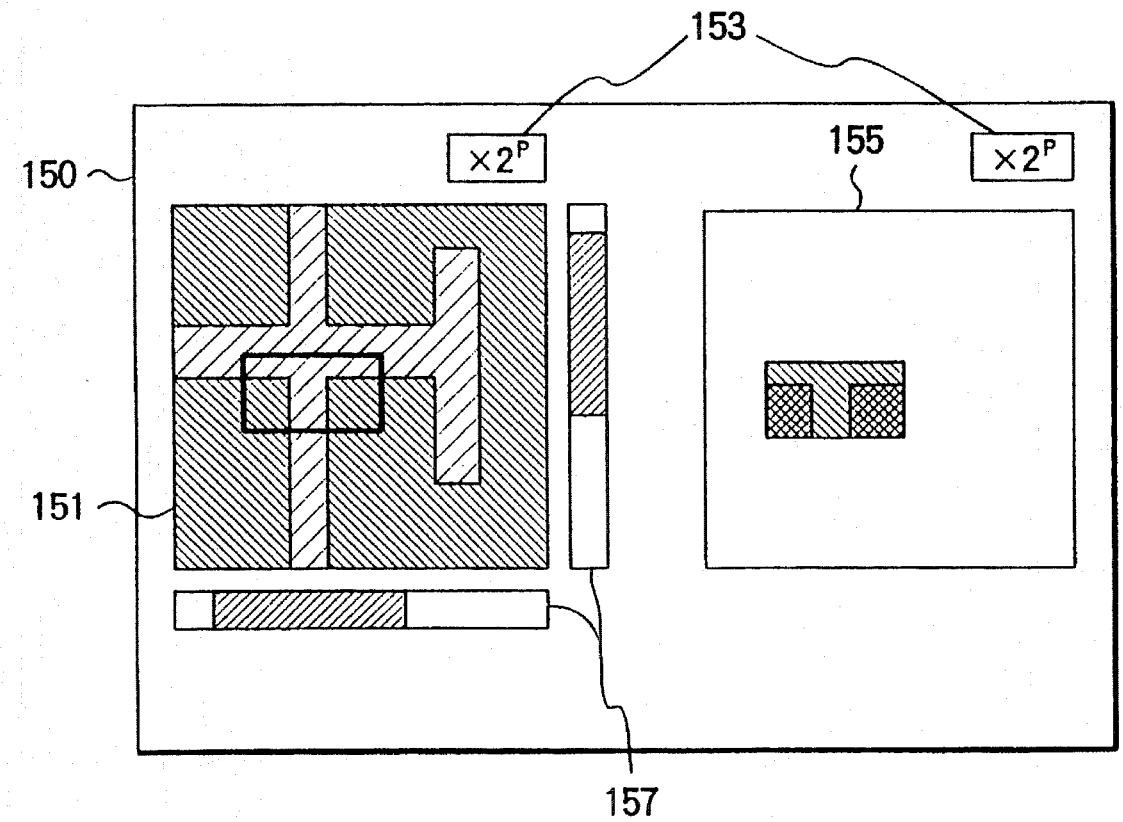
FIG. 14 illustrates an example of a picture of an area to be treated as displayed in the real time.

Further, as in step 143, by displaying the observation data in the picture in real time, the change of treatment can be adapted to be observed. FIG. 14 illustrates an example of a display picture in which the observation data in the treatment mode are displayed in real time. In the display picture 150 of FIG. 14, a picture 151 is a designated picture of the area to be treated. A picture 157 indicates an observation area. A picture 153 indicates a magnification of observation. A picture 155 indicates an image observed in the treatment mode.

Figure 15:
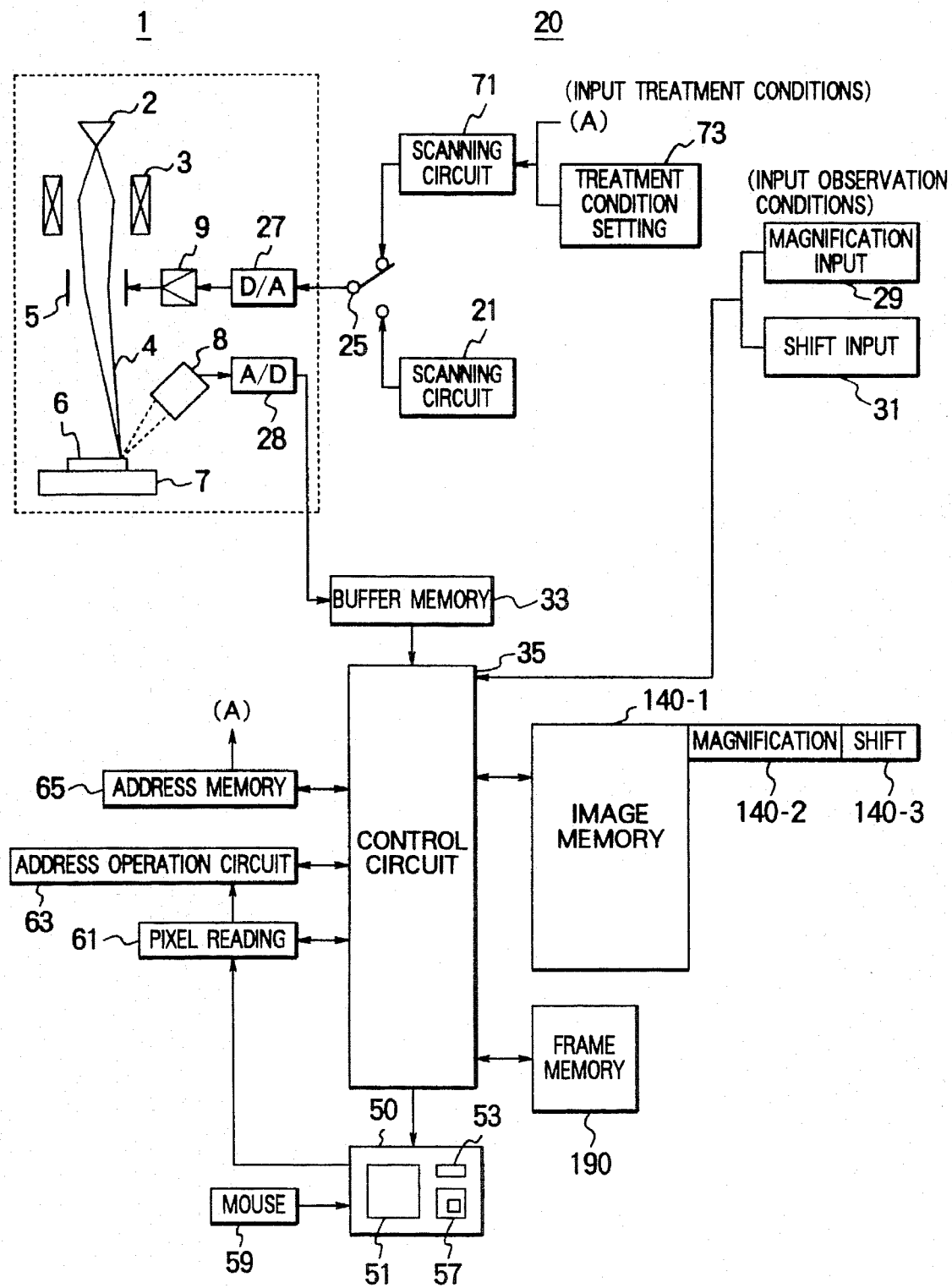
FIG. 15 schematically illustrates a treatment and observation apparatus according to a third embodiment of the present invention.

FIG. 15 schematically illustrates a treatment and observation apparatus according to another embodiment. Like elements to those of FIG. 1 are designated by like reference numerals and description thereof is partially omitted.

In the embodiment, the area (shown in the picture 51-1 of FIG. 5) of the sample corresponding to the reference image of the preceding embodiment is previously observed with the maximum resolution or the resolution near thereto and the observed data are stored in a memory 140-1. The addresses of the memory correspond one-to-one to the addresses of the sample. The large observation magnification is stored in a memory 140-2 and (0, 0) is stored as the shift data in a memory 140-3. The memory capacity of the image memory 140-1 is very large and all addresses thereof cannot be caused to correspond one-to-one to the addresses of pixels on the picture of a conventional display unit. A control circuit 35 compresses data in the image memory 140-1 and stores the compressed data in a frame memory 190. The addresses in the frame memory correspond one-to-one to the addresses in the image memory 140-1. The buffer memory 33 can be used as the image memory.

As the reference image, data in the frame memory 190 are displayed in the picture. Displayed contents are identical with FIG. 5.

When an area to be magnified in the reference image is designated in the same manner as in the preceding embodiment on the basis of the origin and the magnification in order to retrieve the reference point for treatment (when the portion surrounded by the broken line of FIG. 5, for example, is designated), the control unit 35 calculates addresses (which are equal to addresses in the image memory 140-1) on the sample contained in the area. Data in the addresses are read out from the image memory 140-1 and displayed on the picture (display on the picture is identical with FIG. 7). Similarly, the picture of FIG. 9 is obtained. The reference point of the area to be treated can be designated from these Figures and the treatment mode can be carried out on the basis of the reference point in the same manner as in the embodiment of FIG. 1.

According to the embodiment, since observation is first performed with the maximum magnification, time is required for the observation and a large storage capacity is required for the image memory 140-1, while increased information is obtained from the observation and accordingly the application range is spread.

An application example is now described.

Figure 16:
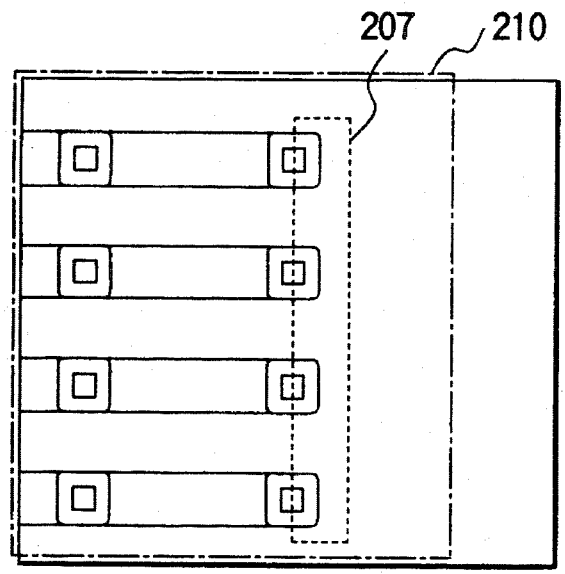
FIG. 16 illustrates a sample observed by using the apparatus of the third embodiment.

A sample is shown in FIG. 16 and an area to be treated is shown by a box indicated by broken line 207 of FIG. 16. A procedure for positioning the area to be treated is described in the following (1) to (3).

(1) The whole of a somewhat large area of 80 μm square (in a box indicated by one-dot chain line 210 of FIG. 16) including the rectangular area to be treated is digitally scanned with the beam and its high-resolution SIM image is stored in an image memory (2048×2048 pixels).

Figure 17:
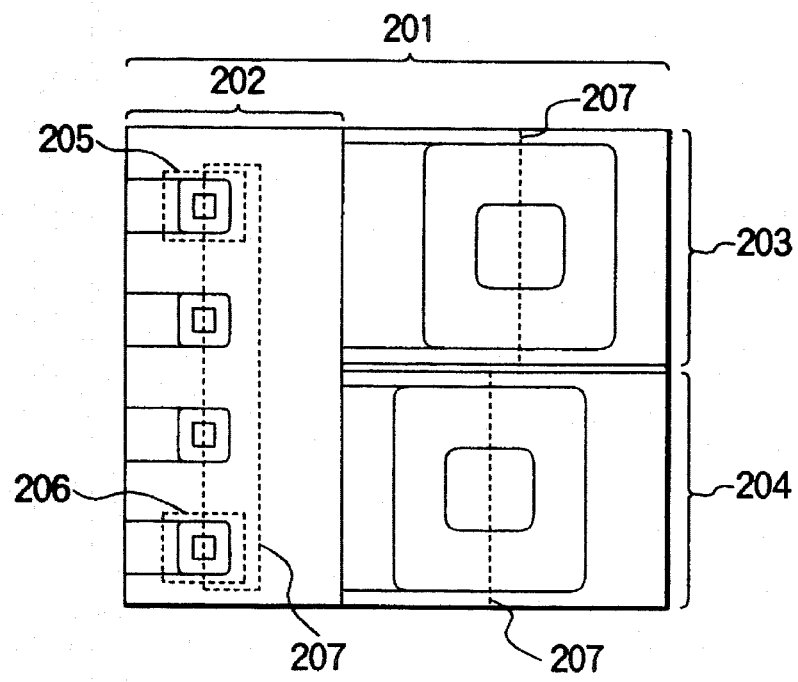
FIG. 17 illustrates an example of a displayed picture in the apparatus of the third embodiment.

(2) The image memory data are used to simultaneously display three SIM images 202, 203 and 204 having different magnification on a picture 201 (refer to FIG. 17) of a display unit divided into multiple windows. The SIM image 202 displays the whole area to be treated with low magnification and displays part of the memory image data compressed by half with 1024×480 pixels in length and width. On the other hand, the SIM images 203 and 204 are images magnified with the high magnification of 1.75×1.75 and displayed by 512×720 pixels of areas 205 and 206 taken out from the memory image data, respectively. The high-magnified SIM images 203 and 204 of the latter are 3.5×3.5 times larger on the display picture 201 than the low-magnified SIM image 202 of the former. The magnitude of the window can be varied and its maximum is the display screen of the display unit. Further, the high-magnified SIM image can be moved to a desired location in the image memory.

(3) The area 207 to be treated has a size of about 10×75 μm$^2$ and is rectangular. A section to be treated and desired to be observed comprises four contact holes arranged vertically. It is necessary to perform setting with high positional accuracy so that the left side of the rectangle passes through the center of all contact holes. It is considered that when the high-magnified SIM images 203 and 204 for the uppermost contact hole and the lowermost contact hole are used to align the left side of the area (rectangle) 207 to be treated with the center of both of the contact holes, the left side of the area to be treated is aligned with the center of all contact holes. Writing, movement, magnification and modification onto the box of the area to be treated (rectangle) can be made from any image of the SIM images 202, 203 and 204, and display of the boxes is interlocked with each other on all of the SIM images.

The area-to-be-treated position setting operation is carried out by a mouse since the picture of the display unit is controlled by a computer (not shown). When a focused ion beam having a beam diameter of 0.1 μm is used for the treatment for finishing, the treatment position setting accuracy in the low-magnified SIM image 202 and the high-magnified SIM images 203 and 204 are about 0.4 and 0.1 μm, respectively, and in the hole section treatment of the embodiment the high-magnified images 203 and 204 are required.

The magnification function of the image data of the procedure (2) has the following effects. One pixel on the picture of the display unit (CRT) is about 0.3 mm and it may be difficult to set the treatment position with accuracy of about one pixel using the naked eye. However, as in the above embodiment, for example, one pixel is as larger as about 0.6 mm with magnification of about 2×. By utilizing the magnified image, the treatment position accuracy can be increased to the resolution of about one pixel at the conversion of the high-resolution SIM image. The diameter of the beam is smaller than about one pixel in the SIM image that is not magnified.

In the above example, three SIM images are displayed in one display unit simultaneously, while three SIM images may be displayed in three display units separately. However, a plurality of display units are then required. In the embodiment, the images for setting the area to be treated use the SIM images using secondary electrons of secondary particles emitted from the sample are irradiated with a scanning focused ion beam, while secondary ions may be used as secondary particles. From the viewpoint of the signal intensity, generally, SIM images with good S/N ratio are obtained from secondary electrons as compared with secondary ions. However, secondary ions have strong element dependency of the emission intensity thereof as compared with secondary electrons, and thus secondary ions may be advantageous depending on an object to be treated.

Further, as the focused ion beam, electrons can be used in addition to the ions in the above embodiment. By introducing a reactive gas of fluorine or chlorine in the vicinity of the surface of the sample irradiated with the beam of ions or electrons, the beam-induced etching can be performed. In this case, it is advantageous that the etched particles are not left and the etching speed is increased. In the depositing work or treatment, gas containing an element to be deposited is locally blown on the vicinity of the surface of the sample irradiated with the beam by a nozzle to thereby effect the beam induced deposit. In another embodiment, powdered tungsten hexacarbonyl ($W(CO)_6$) as a material for the gas source may be heated to about 50° C. and steam pressure gas thereof blown on the sample to deposit tungsten. The metal deposition may be used in installation of local wiring of a device.

According to the foregoing, in the treatment process of maskless etching or deposition for a minute device such as a semiconductor device using a focused beam, even if the area to be treated has an elongated shape such as a rectangle, the area to be treated can be set with high positional accuracy. Accordingly, a high degree of treatment can be attained.

We claim:

1. A treatment and observation apparatus using a scanning probe, comprising:

means for holding a sample;

means for positioning a probe at a point on said sample designated by a two-dimensional address with respect to a predetermined reference point;

means for stepwise moving the position of said probe in response to a change of the address on said sample to thereby scan said probe on said sample;

means for displaying an image of said sample on a display screen, wherein addresses for pixels on said display screen correspond to addresses on said sample to which said probe is positioned;

detecting means for detecting signals received from said probe, said signal being produced in accordance with positioning of said sample with respect to said probe;

first designating means for designating, on said display screen, an area to be observed, and for scanning, with said probe, a first area on said sample corresponding to said area to be observed to produce an image signal to be detected by said detecting means, said designation of an area to be observed comprising a first magnification and first shift data;

first image forming means for forming an image based on said image signal thus produced;

means including a memory for storing at least two images formed by said first image forming means along with said designation of an area to be observed;

second designating means for designating, on said display screen, an area to be treated, and for scanning, with said probe, a second area on said sample corresponding to said area to be treated under given conditions to treat said second area on said sample;

means for combining said at least two images stored in said memory and having the same magnification to form a combined image by referencing said designation of an area to be observed;

means for displaying scrollably said combined image on said display screen; and third designating means for designating, on said display screen, an area to be displayed in said combined image, said designation of an area to be displayed comprising a second magnification and second shift data.

2. An apparatus according to claim 1, wherein said probe is a focused ion beam.

3. An apparatus according to claim 2, wherein said first magnification corresponds to a step width of said probe and is expressed by $N^n$ where N is a positive integer and n is 0 or a positive integer.

4. An apparatus according to claim 2, wherein said first magnification corresponds to a step width of said probe and is expressed by $2^n$ where n is 0 or a positive integer.

5. An apparatus according to claim 2, further comprising:

second image forming means for forming an image of said area to be treated on the basis of a signal obtained when said area to be treated is irradiated with said ion beam for a treatment of the area to be treated.

6. An apparatus according to claim 5, further comprising:

means for displaying said image of said area to be treated on said display screen simultaneously with said combined image.

7. An apparatus according to claim 6, wherein said means for displaying said image of said area to be treated displays a treatment state of said area to be treated in real time.

8. A controller for controlling a treatment and observation apparatus including means for holding a sample; means for positioning a probe at a point on said sample designated by a two-dimensional address with respect to a predetermined reference point; means for stepwise moving the position of said probe in response to a change of the address on said sample to thereby scan said probe on said sample; means for displaying an image of said sample on a display screen, wherein addresses for pixels on said display screen correspond to addresses on said sample to which said probe is positioned; detecting means for detecting signals received from said probe, said signal being produced in accordance with positioning of said sample with respect to said probe; first designating means for designating, on said display screen, an area to be observed, and for scanning, with said probe, a first area on said sample corresponding to said area to be observed to produce an image signal to be detected by said detecting means, said designation of an area to be observed comprising a first magnification and first shift data; means for forming an image based on said signal thus produced; first storing means including a memory for storing said image formed by said first image forming means along with said designation of an area to be observed; and second designating means for designating on said display screen, an area to be treated, and for scanning, with said probe, a second area on said sample corresponding to said second area to be treated under given conditions to treat said second area on said sample;

said controller comprising:

second storing means including a memory for storing at least two of said images together with said designation of an area to be observed;

means for combining said at least two images stored in said memory of said second storing means and having the same magnification to form a combined image by referencing said designation of an area to be observed;

means for displaying scrollably said combined image on said display screen; and third designating means for designating, on said display screen, an area to be displayed in said combined image, said designation of an area to be displayed comprising a second magnification and second shift data.

9. An apparatus according to claim 8, wherein said probe is a focused ion beam, and wherein said first magnification corresponds to a step width of said probe and is expressed by $2^n$, where n is 0 or a positive integer.

10. An apparatus according to claim 8, further comprising:

second image forming means for forming an image of said area to be treated on the basis of a signal obtained when said area to be treated is irradiated with said ion beam for a treatment of the area to be treated.

11. An apparatus according to claim 10, further comprising:

means for displaying said image of said area to be treated on said display screen simultaneously with said combined image.

12. An apparatus according to claim 11, wherein said means for displaying the image of said area to be treated displays a treatment state of said area to be treated in real time.

13. A method of controlling a treatment and observation apparatus including means for holding a sample; means for positioning a probe at a point on said sample designated by a two-dimensional address with respect to a predetermined reference point; means for stepwise moving the position of said probe in response to a change of the address on said sample to thereby scan said probe on said sample; means for displaying an image of said sample on a display screen, wherein addresses for pixels on said display screen correspond to addresses on said sample to which said probe is positioned; detecting means for detecting signals received from said probe, said signal being produced in accordance with positioning of said sample with respect to said probe; first designating means for designating, on said display screen, an area to be observed, and for scanning, with said probe, a first area on said sample corresponding to said area to be observed to produce an image signal to be detected by said detecting means, said designation of an area to be observed comprising a first magnification and first shift data; means for forming an image based on said signal thus produced; means including a memory for storing at least two images formed by said first image forming means along with said designation of an area to be observed; second designating means for designating on said display screen, an area to be treated, and for scanning, with said probe, a second area of said sample corresponding to said second area to be treated under given conditions to treat said second area on said sample;

said method comprising the steps of:

storing at least two of said images together with said designation of an area to be observed;

combining said at least two images in a same magnification to form a combined image by referencing said designation of an area to be observed;

displaying scrollably said combined image on said display screen; and designating, on said display screen, an area to be displayed in said combined image, said designation of an area to be displayed comprising a second magnification and second shift data.

14. An apparatus according to claim 1, wherein said second magnification and second shift data are controlled to be equal to said first magnification and first shift data, respectively.

15. An apparatus according to claim 8, wherein said second magnification and second shift data are controlled to be equal to said first magnification and first shift data, respectively.

16. A display device for displaying an image in accordance with stored image data of a subject to be scanned by a scanning probe, comprising:

first storing means for storing first image data of a subject to be observed, said first image data being obtained with said scanning probe at a first magnification;

second storing means for storing second image data corresponding to a region of interest of said subject identified by selecting coordinates of said subject, said second image data being calculated by magnifying a part of said first image data by a second magnification, said part corresponding to said region of interest; and third storing means for storing third image data of said region of interest identified by said selected coordinates, said third image data being obtained by scanning said region of interest with said probe at a third magnification greater than said first magnification, said third image data representing an image having a higher resolution than that represented by both said first image data and said second image data.

17. A display device according to claim 16, further comprising means by which an operator designates said region of interest on a display on which an image is displayed in accordance with said first image data.

18. A display device according to claim 16, wherein said second magnification substantially equals said third magnification.

19. A display device for displaying an image in accordance with stored image data of a subject to be scanned by a scanning probe, comprising:

a first store in which are stored first image data of a subject to be observed, said first image data being obtained with said scanning probe at a first magnification;

a second store in which are stored second image data corresponding to a region of interest of said subject identified by selecting coordinates of said subject, said second image data being calculated by magnifying a part of said first image data by a second magnification, said part corresponding to said region of interest; and a third store in which are stored third image data of said region of interest identified by said selected coordinates, said third image data being obtained by scanning said region of interest with said probe at a third magnification greater than said first magnification, said third image data representing an image having a higher resolution than that represented by both said first image data and said second image data.

20. A display device according to claim 19, further comprising an input device by which an operator designates said region of interest on a display on which an image is displayed in accordance with said first image data.

21. A display device according to claim 19, wherein said second magnification substantially equals said third magnification.

22. A method for displaying an image of a subject, comprising the steps of:

scanning said subject with a probe at a first magnification to display a first image of a scanned region of the subject on a display screen, and to store first image data corresponding to said first image in a first store;

designating, on said display screen on which said first image is displayed, a region of interest of said subject in said scanned region;

retrieving a part of said first image data having said first magnification from said first store, and processing said retrieved first image data to calculate and display a second image on said display screen, said second image being a magnified image of said region of interest having a second magnification, and said part corresponding to said region of interest; and scanning said region of interest with said probe at a third magnification to display a third image thereof, said third image having a higher resolution than both said first and second images.

23. A method according to claim 22, wherein said second magnification substantially equals said third magnification.

24. A treatment apparatus comprising:
first storing means for storing first image data of a subject to be observed, said first image data being obtained with said scanning probe at a first magnification;
second storing means for storing second image data corresponding to a region of interest of said subject identified by selecting coordinates of said subject, said second image data being calculated by magnifying a part of said first image data by a second magnification, said part corresponding to said region of interest;
third storing means for storing third image data of said region of interest identified by said selected coordinates, said third image data being obtained by scanning said region of interest with said probe at a third magnification greater than said first magnification, said third image data representing an image having a higher resolution than that represented by both said first image data and said second image data;
display means including a display screen for displaying images on said display screen;
means by which an operator employs said display means to designate, on said display screen on which is displayed an image constructed in accordance with said third image data, an area to be treated in said subject; and
means for treating the area thus designated.

25. A treatment apparatus according to claim 24, further comprising means by which said operator employs said display means to designate, on said display screen on which an image constructed in accordance with said first image data is displayed, said region of interest.

26. A treatment apparatus according to claim 24, wherein said second magnification substantially equals said third magnification.

27. A method for treating a subject, comprising the steps of:
scanning said subject with a probe at a first magnification to display a first image of a scanned region of the subject on a display screen, and to store first image data corresponding to said first image in a first store;
designating, on said display screen on which said first image is displayed, a region of interest of said subject in said scanned region;
retrieving a part of said first image data having said first magnification from said first store, and processing said retrieved first image data to calculate and display a second image on said display screen, said second image being a magnified image of said region of interest having a second magnification, and said part corresponding to said region of interest;
scanning said region of interest with said probe at a third magnification to display a third image thereof, said third image having a higher resolution than both of said first and second images;
designating, on said display screen on which said third image is displayed, an area to be treated in said subject; and
treating said area thus designated.

28. A method according to claim 27, wherein said second magnification substantially equals said third magnification.

29. A display device comprising:
display means for displaying images on a display screen;
means for obtaining a first image of a subject to be observed by a scanning probe, to display said first image on said display screen by employing said display means;
means for forming a second image which is constructed and magnified at a first magnification by processing a region within said first image selected by an operator through said display means, to display said second image on said display screen;
means for scanning said region with said probe at said first magnification to form a third image having a higher resolution than that of both of said first and second images;
means for scrolling a fourth image which is constructed and magnified at said first magnification by processing through said first image; and
means for substituting said third image for a corresponding region of said fourth image, whereby said third image and said fourth image are scrolled integrally.

30. A method for scrolling an image on a display, comprising the steps of:
obtaining a first image of a subject to be observed by a scanning probe to display said first image on a display;
forming a second image which is constructed and magnified at a first magnification by processing a region within said first image selected by an operator through said display;
displaying said second image;
scanning said region with said probe at said first magnification to display and form a third image having a higher resolution than both of said first and second images;
scrolling a fourth image which is constructed and magnified at said first magnification by processing through said first image; and
substituting said third image for a corresponding region of said fourth image, whereby said third image and said fourth image are scrolled integrally.

31. A treatment apparatus comprising:
display means for displaying images on a display screen;
means for obtaining a first image of a subject to be observed by a scanning probe, to display said first image on said display screen by employing said display means;
means for forming a second image which is constructed and magnified at a first magnification by processing a region within said first image selected by an operator through said display means, to display said second image on said display screen;
means for scanning said region with said probe at said first magnification to form a third image having a higher resolution than both of said first and second images;
means for scrolling a fourth image which is constructed and magnified at said first magnification by processing through said first image;
means for substituting said third image for a corresponding region of said fourth image, whereby said third image and said fourth image are scrolled integrally;
means by which said operator employs said display means to designate an area to be treated in said subject, on the display screen on which said third image is displayed, said area to be treated being designated on said third image; and means for treating the area designated on said third image.

32. A method for treating a subject, comprising the steps of:

obtaining a first image of a subject to be observed by a scanning probe to display said first image on a display;

forming a second image which is constructed and magnified at a first magnification by processing a region within said first image selected by an operator through said display;

displaying said second image;

scanning said region with said probe at said first magnification to form and display a third image having a higher resolution than both of said first and second images;

scrolling a fourth image which is constructed and magnified at said first magnification by processing through said first image;

substituting said third image for a corresponding region of said fourth image, whereby said third image and said fourth image are scrolled integrally;

designating an area to be treated in said subject, on the display on which said third image is displayed, said area to be treated being designated on said displayed third image; and treating said area designated on said third image.

* * * * *